United States Patent [19]
Franseen et al.

[11] Patent Number: 5,158,452
[45] Date of Patent: Oct. 27, 1992

[54] ORTHODONTIC APPLIANCE MOUNTING BASE

[75] Inventors: Steven A. Franseen, Denver; Jeffrey A. Peterson, Aurora, both of Colo.

[73] Assignee: RMO, Inc., Denver, Colo.

[21] Appl. No.: 649,594

[22] Filed: Feb. 1, 1991

[51] Int. Cl.⁵ .................................................. A61C 3/00
[52] U.S. Cl. ........................................... 433/9; 433/24
[58] Field of Search ........................................ 433/8, 9, 24

[56] References Cited

U.S. PATENT DOCUMENTS

| | | | |
|---|---|---|---|
| D. 290,040 | 5/1987 | Kelly | D24/16 |
| 3,969,821 | 7/1976 | Lee, Jr. et al. | 433/9 |
| 4,063,360 | 12/1977 | Waller | 433/9 |
| 4,165,561 | 8/1979 | Miller et al. | 433/9 |
| 4,219,617 | 8/1980 | Wallshein | 433/8 |
| 4,243,386 | 1/1981 | Kawaguchi | 433/9 |
| 4,544,353 | 10/1985 | Maurer et al. | 433/9 |
| 4,604,057 | 8/1986 | Viglietti | 433/9 |
| 4,659,309 | 4/1987 | Merkel | 433/9 |
| 4,661,059 | 4/1987 | Kanno | 433/9 |
| 4,735,569 | 4/1988 | Munk | 433/9 |
| 4,838,786 | 6/1989 | Reher et al. | 433/9 |
| 4,902,224 | 2/1990 | Collins et al. | 433/8 |
| 4,936,773 | 6/1990 | Kawaguchi | 433/9 |

FOREIGN PATENT DOCUMENTS 2534368 8/1975 Fed. Rep. of Germany .......... 433/9
2903768 2/1979 Fed. Rep. of Germany .......... 433/8

OTHER PUBLICATIONS

1983 Rocky Mountain Orthodontics Catalog, pp. 27 and 28.
Ortho Organizers, Inc. Advertisement "Supreme Mini-Twin".

*Primary Examiner*—John J. Wilson
*Attorney, Agent, or Firm*—Sheridan, Ross & McIntosh

[57] ABSTRACT

Rails (38) project from a mesial edge (40) and a distal edge (42) of a base (28) of an orthodontic appliance (30) forming a gap between the base (28) and a surface (32) of a tooth (34). At least one post (44) projects from the base (28) between the rails (38). The rails (38) and post (44) are dimensioned to substantially preclude post-/tooth contact and reduce the likelihood of appliance detachment from a curved tooth surface. The posts (44) are formed to resist shear forces associated with mastication and to facilitate the smooth flow of bonding material about the posts (44) when the base (28) is pressed against a tooth surface (32) during bonding.

33 Claims, 2 Drawing Sheets

ORTHODONTIC APPLIANCE MOUNTING BASE

TECHNICAL FIELD OF THE INVENTION

This invention relates in general to orthodontic appliances, and in particular to mounting bases for attaching orthodontic appliances to the surface of a tooth.

BACKGROUND OF THE INVENTION

Orthodontic appliances are often attached to a labial or lingual tooth surface by using a bonding material such as cement which is rigid upon setting Typically, in one step of the attachment process, the appliance base is coated with bonding material and then the base is pressed against a tooth surface. It is desirable, of course, that the resulting bond be strong enough to withstand forces exerted on the appliance during treatment. However, as is well known, failure of any device first occurs at the weakest point, and in the application of orthodontic devices to the surface of a tooth, the weakest point will be in the bond by design. As is well known, orthodontic adhesives are specifically tailored to provide this weakest point for the controlled debonding at the end of treatment. However, the problem typically is to select an adhesive having adequate strength for treatment that will still allow removal of the bracket at the end of treatment without causing damage to the tooth.

While there are many forces that act on the appliance, the resulting tensile/compressive forces are of interest herein. Due to the curvature, both mesio-distally and occlusal-gingivally, of tooth surfaces, many prior appliances have been susceptible to stress on the bond from tensile/compressive forces which may ultimately cause the bond to break resulting in appliance detachment. For example, a compressive force along one edge of the appliance will be transmitted directly to the bond. If there is a pivot point between the opposite edges of the appliance due to tooth curvature or other surface incongruities, the compressive force on the one edge may cause the tensile force on the bond near the opposite edge to be so great as to detach the appliance. Therefore, any place where support to resist a force is provided by the bond rather than part of the base, a failure is more likely to occur. In order to reattach the appliance, an unnecessary visit to the orthodontist is required and treatment is interrupted.

A specific example of this problem with tensile/compressive forces is illustrated by the tendency of an appliance to detach when a patient bites into a resistive food and masticatory forces are applied to the appliance. The masticatory forces tend to compress the bond near one edge of the base and tension the bond near the other edge. The resulting shear forces on the bond may cause the appliance to peel away from the tooth surface beginning at the edge in tension.

Another problem with known mounting bases is a tendency for air pockets to remain in the bonding material after application. Many known appliance bases are fabricated to include holes or recesses and/or for use with meshes in attempts to increase the bonding surface area of the appliance. However, it is difficult to apply the bonding material to expel air pockets adjacent to such surfaces in many appliances. For example, when pressed against a tooth surface, these base designs do not accommodate air pocket evacuation responsive to the compressive forces communicated through the bonding material due to a lack of open channels for the air and the bonding material to flow.

Orthodontists are typically concerned about the "seating" of the appliance on the tooth. Thus there is a tendency to give the appliance one more push after positioning the appliance on the tooth with adhesive after the adhesive has started to "set" or polymerize. This tendency may cause the base to "rock" and create a weaker bond. Any rocking after polymerization of the adhesive has begun is likely to be detrimental to the overall strength and consistency of the bond.

Additionally, when using ceramic appliances there is a problem with breakage during removal of the appliance after treatment. Any broken parts are possible hazards to the patient and must be carefully removed whether loose in the mouth or stuck on the tooth. Any portions remaining on the tooth surface are especially troublesome as they must be ground off with a diamond burr which may result in damage to the surface of the tooth.

Thus, there is a need for an improved orthodontic appliance base which is stable on tooth surfaces of various curvatures thereby reducing the likelihood of separation therefrom and the resulting appliance failure. In addition, there is a need for an orthodontic appliance base which provides greater resistance to masticatory forces. There is also a need for an orthodontic appliance base which provides a large bonding surface area while reducing the likelihood that air pockets will remain between the bonding material and the base upon application to a tooth.

SUMMARY OF THE INVENTION

The present invention comprises an orthodontic appliance base which substantially reduces problems with prior bases. The inventive base is designed to accommodate bracket stability on a variety of tooth morphologies. In addition, the present invention provides bonding surfaces oriented relative to the occlusal plane to yield increased resistance to masticatory forces. The present invention is further designed to permit bonding material to spread relatively evenly and evacuate air pockets throughout the base/bonding material interface when the appliance is coated with bonding material and pressed against a tooth surface, thus reducing the likelihood of detachment.

In accordance with one aspect of the present invention, an orthodontic appliance base is provided with one or more offset posts projecting therefrom. Preferably, the posts comprise side portions oriented such that tangents thereto intersect the lateral and longitudinal axes of the base. In other words, such side portions are, upon application of the base to a tooth, neither parallel nor perpendicular to the gingivally directed masticatory forces. Consequently, the bond shear strength of the appliance is increased by reducing the likelihood of the formation of shear planes.

In accordance with another aspect of the invention, an orthodontic appliance base is provided having slightly arcuate (to accommodate the occlusal-gingival curvature of the tooth) side rails along the mesial and distal edges thereof which project a preselected distance, which is preferably beyond, the aforementioned posts in order to reduce appliance/tooth contact. Thus upon removal of the appliance after treatment, there is less likelihood of portions of the appliance breaking and remaining stuck to the surface of the tooth. In addition, the rails define borders which restrict bonding material flow upon application and tend to cause excess material to flow occlusal-gingivally when the base is pressed against a tooth surface, thereby evacuating air pockets. As will be further appreciated, the noted posts define interconnecting channels which accommodate such evacuation.

In one embodiment, the orthodontic appliance base comprises mesial and distal side rails and a plurality of offset posts positioned intermediate the rails. The rails are slightly arcuate occlusal-gingivally to conform to the typical occlusal-gingival tooth curvature. The rails protrude from the base toward the tooth surface a greater distance than any other portion of the base.

The posts are offset both laterally and longitudinally to reduce the likelihood of formation of a shear plane. Additionally, the posts have side portions formed at an angle, preferably 45°, to the lateral and longitudinal axes of the base. Thus, when bonding material is applied to base and the base is applied to the tooth, channels are available for the excess material to flow through. By providing channels for the bonding material to flow through, the likelihood that air will be trapped between the base and the bonding material is reduced.

The posts provide greater bonding surface area both parallel and perpendicular to forces acting on the appliance and form flow channels in combination with the side rails. The side rails serve to transmit force on the appliance directly to the tooth rather than the bonding material. Therefore, due to the present invention, premature detachment of the base is less likely to occur than with prior art devices.

The combination of the side rails and the posts provide an appliance that is better able to resist forces in the mouth during treatment. Once treatment is over and removal is required, the present invention accommodates removal of the appliance with reduced likelihood of damage to the tooth surface. Since the rails are the only portions of the appliance that directly contact the tooth surface, any breakage of the appliance will likely result in no pieces thereof remaining directly on the tooth surface, i.e., any broken pieces would likely be separated from the tooth surface by the bonding material.

BRIEF DESCRIPTION OF THE DRAWINGS

For a more complete understanding of the invention and for further advantages thereof, reference is now made to the following Detailed Description taken in conjunction with the accompanying Drawings, in which.

DETAILED DESCRIPTION OF THE INVENTION

Figure 1:
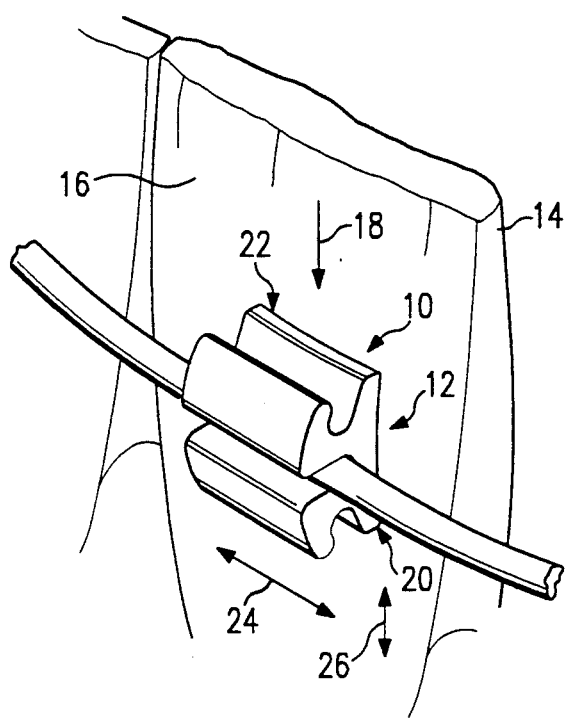
FIG. 1 is a perspective view of a prior art bracket attached to a tooth surface.

Referring first to FIG. 1, a prior art orthodontic bracket is generally identified by the reference numeral 12. The bracket 12 is attached to a tooth 14 by applying bonding material such as cement therebetween and pressing the bracket base 10 against a tooth surface 16. The resulting bond needs to be strong enough to withstand shear such as is associated with gingivally directed masticatory forces, represented by an arrow 18, exerted on the bracket 12 upon chewing. The masticatory forces 18 result in compression of the bond interface along a gingival region 20 of the base 10 and tension of the bonding interface along an occlusal region 22 thereof, and may cause the bracket 12 to peel off the tooth surface 16.

Other conditions can also destroy the bond resulting in detachment of the bracket 12. First, because the tooth surface 16 is curved along both a mesio-distal axis 24 and along an occlusal-gingival axis 26, the base 10 of the bracket 12 is arcuately shaped to generally match the tooth surface 16. However, since there are many different shapes of teeth, it is difficult to produce the base 10, using modern economical mass production techniques, that will match every tooth shape. Thus, one must either settle for a finite number of base shapes that cover some workable percentage of teeth or individually custom design a base for every tooth. Since custom designing is generally not feasible, one must settle for a finite number of shapes and attempt to match the tooth as closely as possible Any mismatch between the base 10 and the tooth 14 creates a potential pivot point about which compressive and tensile forces are transmitted to the cement from the bracket 12. Thus, failure is more likely due to base/tooth mismatch. Additionally, due to the orthodontist's tendency to give the bracket one more push during the polymerization process, pivot points may cause the bracket to rock and thus weaken the overall bond.

Second, air pockets may exist between the cement and the base 10 due to uneven cement application or surface discontinuities thereon. When the bracket 12 is pressed onto the tooth 14, air may not be able to escape, thus weakening the bond by reducing the bonding surface area where polymerization occurs and by creating faults in the cement which are prone to collapse under pressure. These conditions may result in bond failure and detachment of the bracket 10 when masticatory forces 18 are exerted thereon.

Figure 2:
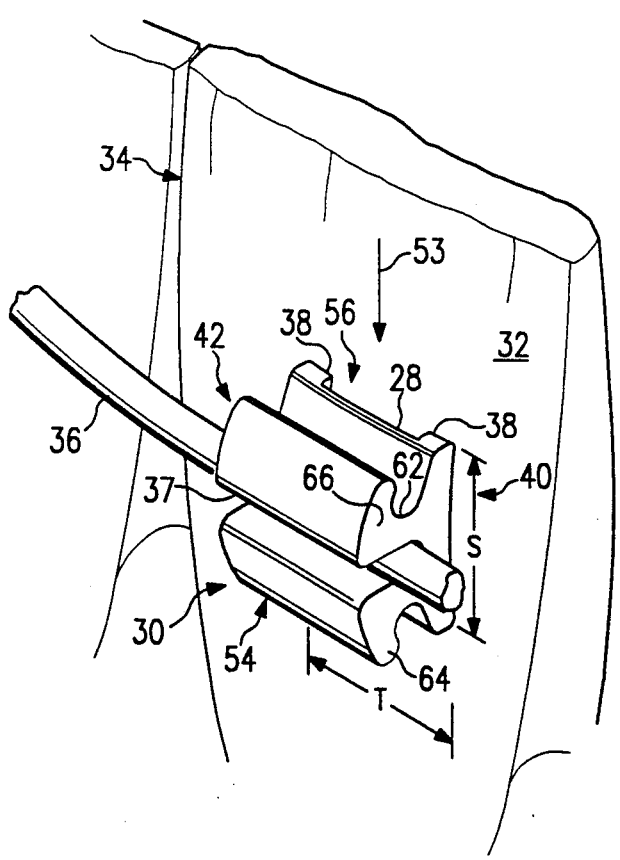
FIG. 2 is a perspective view of an orthodontic appliance, having a base formed in accordance with an embodiment of the present invention, attached to a tooth surface.
Figure 3:
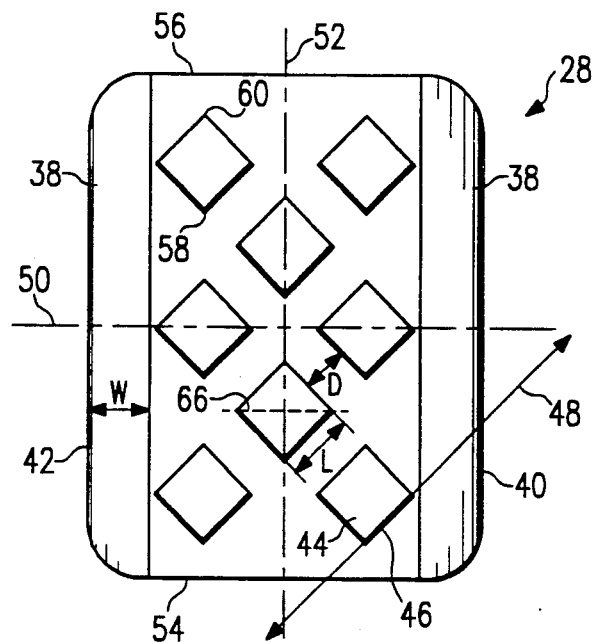
FIG. 3 is a bottom plan view of an orthodontic appliance having a base formed in accordance with the present invention.

In FIGS. 2-4, like items are identified by like and corresponding numerals for ease of reference. Referring first to FIG. 2, a perspective view of an appliance, having a base 28 formed in accordance with an embodiment of the present invention, is generally identified by the reference numeral 30. The appliance 30 comprises, for example, bondable lingual retainers, orthodontic brackets such as edgewise brackets (shown), light wire brackets, buccal tubes, and etc., having the base 28 for attachment to a surface 32 of a tooth 34. The appliance 30 is adapted to receive an archwire 36 in a slot 37 to apply corrective forces to the tooth 34. The appliance 30 may comprise any suitable material such as stainless steel, ceramic, plastic or a composite material.

The appliance 30 has an at least slightly arcuate mesial edge 40, an at least slightly arcuate distal edge 42, an at least slightly arcuate occlusal edge 56, and an at least slightly arcuate gingival edge 54. For example, the mesial and distal edges 40-42 may have a radius of curvature of approximately 0.433 inches over a length of 0.140 inches and the occlusal and gingival edges 56-54 may have a radius of curvature of approximately 0.140 inches over a width of 0.120 inches. The radius of curvature for each edge is selected to accommodate a range of teeth for which the base is designed.

As shown in FIG. 2, the appliance 30 is fixed to the surface 32 which is the labial surface of the tooth 34, however, it is to be understood that the appliance 30 may also be applied to the lingual surface of the tooth 34. The appliance 30 has a pedestal 62 which is integrally fixed to the base 28. A pair of wing tips 64 and 66 protrude from the pedestal 62. As is well known in the art, a retaining device such as, for example, a ligature wire (not shown) is attached around the wing tips 64 and 66 to retain the wire 36 in the slot 37.

Referring to FIG. 3, a bottom plan view of the appliance 10 is illustrated. The base 28 includes rails 38 projecting from the mesial edge 40 and the distal edge 42 thereof and at least one post 44 projecting therefrom. The rails 38 are positioned on the mesial edge 40 and the distal edge 42 because the occlusal-gingival curvature of a tooth is generally less from tooth to tooth than is the mesio-distal curvature. Thus the appliance 10 will be adapted for use on a wider variety of teeth. The posts 44 are arranged in an offset pattern along both a lateral axis 50 and a longitudinal axis 52 of the base 28 to reduce the likelihood of the formation of a shear plane. The post 44 has side portions 46 oriented such that a tangent 48 thereto intersects the lateral axis 50 and the longitudinal axis 52. The post 44 provides increased bonding surface area both perpendicular and parallel to forces acting on the appliance 10.

Although the illustrated posts 44 are substantially diamond shaped and are inclined approximately 45° relative to the lateral axis 50 of the base 28, it is to be understood that other shapes such as circles, ellipses, polygons, rhomboids or stars could be utilized. Similarly, other post orientations could be utilized. However, posts 44 that are offset and have side portions 46 which are not perpendicular to the gingivally directed masticatory forces indicated on FIG. 2 by an arrow 53 are more likely to resist failure. The posts 44 have, for example, a side length L of approximately 0.010 inches and a minimum distance D between adjacent posts of approximately 0.010 inches.

Figure 4A:
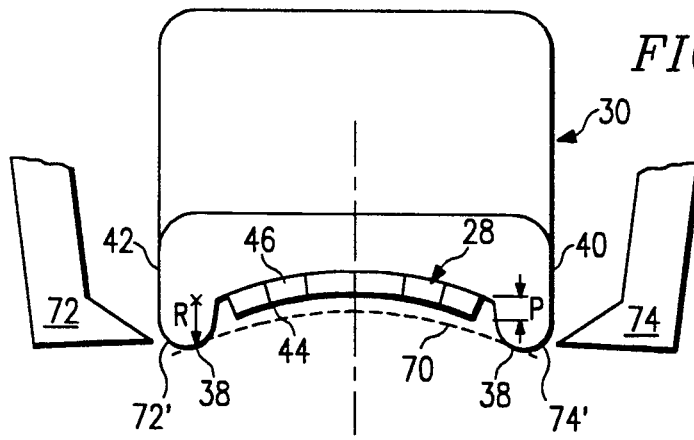
FIGS. 4A and 4B are front (occlusal) elevational view of an orthodontic appliance having a base formed in accordance with the present invention.
Figure 4B:
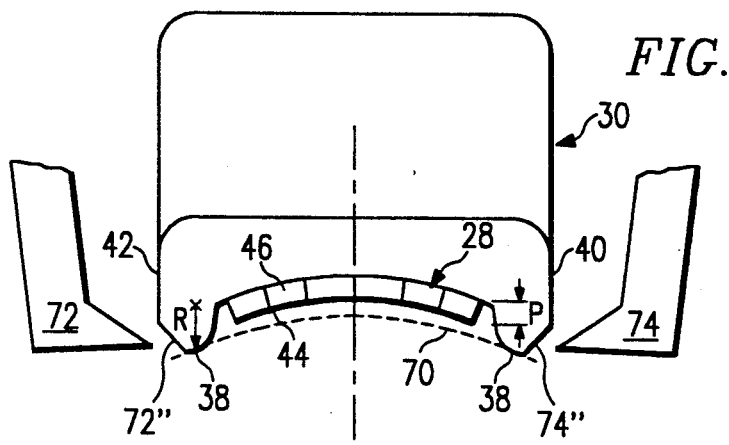

Referring to FIGS. 4A and 4B, an occlusally oriented elevational view of the appliance 30 is illustrated. In an important aspect of the present invention, the rails 38 extend a distance R from the base 28 which is greater than a distance P of the posts 44, thereby substantially precluding post/tooth contact and reducing the likelihood of forming pivot points therebetween. The rails 38 and posts 44 can be dimensioned to generally accommodate the curvature of the tooth surface 32 (see FIG. 2) for which the appliance 30 is designed. In one embodiment, the rails 38 extend the distance R which may be, for example, approximately 0.012 inches and the posts 44 extend the distance P which may be, for example, approximately 0.008 inches. The rails 38 may have a width W (see FIG. 3) of approximately 0.015 inches and, in an important aspect of the present invention, form purchase points which may comprise, for example, rounded edges (see FIG. 4A) or chamfered edges (see FIG. 4B) to facilitate removal when treatment is finished.

Due to the formation of purchase points 72', 74' and 72", 74", it is possible to insert a debonding tool between the surface of the tooth, as indicated by dashed line 70, and the rails 38. In FIG. 4A, the beaks 72 and 74 of a debonding plier, such as is available, for example, from ETM Corporation, are shown about to be used to remove the appliance 30. In comparison to prior art bases, the appliance 30 and the rails 38 will direct debonding forces away from the surface of the tooth by forming the purchase points 72', 74' and 72", 74", for engagement by the beaks 72 and 74 of the debonding plier. In prior appliances, removal attempts (after completion of treatment) may result in breaking of the appliance (especially if the appliance comprises ceramic) rather than separation from the tooth thus leaving jagged edge on the tooth. Any remaining portions of the appliance must then be ground off risking the possiblity of damage to the tooth. With the present invention, even if the appliance 30 should break, the force of the beaks 72 and 74 of the debonding plier would lift the pieces up and away from the surface of the tooth 70. Additionally, since the only portion of the appliance 30 touching the tooth is the rails 38, there is less material that could remain on the tooth after debonding (should fracture of the appliance occur).

The rails 38 also serve to contain the cement when the base 28 is pressed against the tooth surface 32. When the base 28 is pressed against the surface 32, the cement therebetween begins to spread. The rails 38 substantially prevent the bonding material from escaping across the mesial edge 40 and the distal edge 42 of the base 28. Consequently, the cement tends to flow occlusal-gingivally and excess cement escapes at the occlusal edge 56 and the gingival edge 54 of the base 28 due to the channels formed between the posts 44.

In the illustrated embodiment, the combinative post-/rail benefits are achieved. In addition to providing a bonding surface with increased resistance to shear associated with mastication, the side portions 46 of the posts 44 are oriented to facilitate the occlusal-gingival flow of the cement during positioning on the tooth 34. As the base 28 is pressed against the surface 32, the bonding material flows between and about the posts 44 before the excess escapes. Air pockets are less likely to remain than in a base constructed according to the prior art as a result of the posts 44 and the spaces therebetween which provide a direct path for the air to escape. For example, if the posts 44 were oriented so that side portions 46 were parallel to the edges of the base 28, the bonding material might flow through occlusal-gingival channels between the posts 44 and leave air pockets in mesio-distal channels.

Although in FIGS. 2 and 4 the orthodontic appliance base is shown as an integral portion of an orthodontic bracket, it is to be understood that the base could be used with other orthodontic appliances. For example, the base may be formed as a separate pad and welded or brazed to a further orthodontic appliance.

Although the present invention has been described with respect to specific embodiments thereof, various changes and modifications may be suggested to one skilled in the art and it is intended that the present invention encompass such changes and modifications as fall within the scope of the appended claims.

What is claimed is:

1. A base for attaching an orthodontic appliance to a tooth surface, at least a portion of the base having an occlusal-gingival curvature, comprising:

a plurality of spaced apart posts projecting from the base towards the tooth surface to define interconnecting channels between peripheries of said posts, wherein each of said posts has a projecting end, said projecting ends collectively defining a mesial-distal arcuate surface; and rails projecting from the base towards the tooth along opposite edges of the base, wherein said rails project further from the base than said posts.

2. The base of claim 1, wherein said space between said posts allows excess bonding material to flow along the base between said posts when the base is pressed against the tooth surface.

3. The base of claim 1, wherein said posts are substantially diamond shaped, said posts being oriented such that edges thereof form angles of approximately 45° relative to said lateral axis.

4. The base of claim 1, wherein said posts comprises a rhomboid shape.

5. The base of claim 1, wherein said posts comprise a polygon shape.

6. The base of claim 1, wherein said posts comprise arcuate side portions.

7. The base of claim 1, further comprising:
rails projecting from the base towards the tooth surface along opposite edges of the base.

8. The base of claim 7, wherein said posts define at least one channel which extends between said rails.

9. The base of wherein said rails further comprise:
purchase points to allow insertion of a debonding plier between said rails and the tooth surface.

10. The base of claim 1, wherein the width of each said space between adjacently located said posts is at least equal to a smallest width of said posts.

11. The base of claim 1, wherein said projecting ends of said posts collectively define a gingival-occlusal arcuate surface.

12. The base of claim 1, wherein said posts define at least one channel which extends from a first edge portion of the base to a second edge portion of the base.

13. The base of claim 1, wherein said posts are positioned along a plurality of substantially parallel axes on the base, said posts on at least one of said axes being offset from said posts on an adjacent said axis.

14. The base of claim 1, wherein a tangent to side portions of said posts intersect both a longitudinal axis and a lateral axis of the base.

15. A base for attaching an orthodontic appliance to a tooth surface, comprising:
rails projecting from the base along opposite edges thereof, said rails forming a gap from the base to the tooth surface between said rails; and
at least one post in said gap projecting from the base towards the tooth surface, wherein a tangent to side portions of said post is transverse to both a longitudinal axis and a lateral axis of the base, wherein said rails project further from the base than does said at least one post.

16. The appliance base of claim 15, wherein excess bonding material tends to flow occlusal/gingivally when the base is pressed against the tooth surface.

17. The appliance base of claim 16, wherein said post has at least one side portion inclined relative to an occlusal plane to facilitate flow of bonding material about said post.

18. The appliance base of claim 15 wherein said rails further comprise:
purchase points to allow a debonding plier to fit between said rails and the tooth surface, wherein likelihood of fracturing the base or damaging the tooth during debonding is reduced.

19. The appliance base of claim 15, wherein said opposite edges comprise metal and distal edges of the base.

20. The appliance base of claim 19, wherein said rails are gingivally/occlusally arcuate.

21. An orthodontic appliance, comprising:
a base for attaching the appliance to a tooth surface, said base having mesial, distal, occlusal, and gingival edges;
a plurality of posts projecting from said base toward said tooth, wherein said posts are substantially diamond shaped with edges of said posts being angularly displaced approximately 45° relative to said occlusal edge of said base; and
rails projecting from said base along opposite edges towards said tooth surface to form a border substantially abutting said tooth surface, wherein said rails extend further from said base than said posts to reduce the likelihood of surface/post contact.

22. The appliance of claim 21, wherein said rails are arcuate along an occlusal-gingival axis to approximately match an occlusal-gingival curvature of said tooth surface.

23. The appliance of claim 21, wherein said posts are arcuate along a mesio-distal axis to approximately match a mesio-distal curvature of said tooth surface.

24. The appliance of claim 21, wherein said posts project from said base a distance of approximately 0.08 inches.

25. The appliance of claim 21, wherein said rails project from said base a distance of approximately 0.012 inches.

26. The appliance of claim 21, wherein said appliance comprises:
ceramic.

27. The appliance of claim 21, wherein said opposite edges comprise said mesial and distal edges of the base.

28. The appliance base of claim 27, wherein said rails are gingivally/occlusally arcuate.

29. A method for reducing the likelihood of orthodontic appliance base detachment from a surface of a tooth due to forces on the appliance, comprising the steps of:
positioning rails which extend toward the tooth from opposite edges of the base directly on the surface of the tooth; and
bonding a portion of the base intermediate said rails to the surface of the tooth with a bonding material which forms an interface therebetween, said intermediate portion comprising one or more posts extending toward the tooth a distance less than said rails.

30. The method of claim 29, further comprising the steps of:
forcing air from between said bonding material and the base, when the base is applied to the surface of the tooth, through channels formed between said posts, wherein the likelihood of air remaining between said bonding material and the base is reduced.

31. A base for attaching at orthodontic appliance to a tooth surface, comprising:
a plurality of spaced apart posts projecting from the base towards the tooth surface to define interconnecting channels between peripheries of said posts; and
rails projecting from the base towards the tooth surface along mesial and distal edges of the base, wherein said rails project further form the base than said posts.

32. The base of claim 31, wherein said rails further comprise:
purchase points to allow insertion of a debonding plier between said rails and the tooth surface.

33. The base of claim 31, wherein a tangent to side portions of said posts intersect both a longitudinal and a lateral axis of the base.

* * * * *